(12) United States Patent
Fillippini

(10) Patent No.: US 11,793,745 B2
(45) Date of Patent: Oct. 24, 2023

(54) TOPICAL SKIN TREATMENT

(71) Applicant: Michael Fillippini, Midwest City, OK (US)

(72) Inventor: Michael Fillippini, Midwest City, OK (US)

(*) Notice: Subject to any disclaimer, the term of this patent is extended or adjusted under 35 U.S.C. 154(b) by 42 days.

(21) Appl. No.: 17/803,133

(22) Filed: Feb. 28, 2022

(65) Prior Publication Data

US 2023/0270661 A1   Aug. 31, 2023

(51) Int. Cl.

| | |
|---|---|
| *A23K 10/30* | (2016.01) |
| *A23K 20/189* | (2016.01) |
| *A61K 8/9778* | (2017.01) |
| *A61Q 19/00* | (2006.01) |
| *A61K 8/98* | (2006.01) |
| *A61K 8/9794* | (2017.01) |
| *A61K 8/04* | (2006.01) |
| *A61K 8/49* | (2006.01) |
| *A61K 8/46* | (2006.01) |
| *A61K 8/73* | (2006.01) |
| *A61K 8/92* | (2006.01) |
| *A61K 8/66* | (2006.01) |

(52) U.S. Cl.
CPC .............. *A61K 8/9778* (2017.08); *A61K 8/04* (2013.01); *A61K 8/466* (2013.01); *A61K 8/498* (2013.01); *A61K 8/66* (2013.01); *A61K 8/736* (2013.01); *A61K 8/922* (2013.01); *A61K 8/9794* (2017.08); *A61K 8/988* (2013.01); *A61Q 19/00* (2013.01)

(58) Field of Classification Search
CPC .............................. A61K 8/9728; A61Q 19/00
See application file for complete search history.

(56) References Cited

U.S. PATENT DOCUMENTS

| | | |
|---|---|---|
| 5,547,672 A | 8/1996 | Xiu |
| 8,524,271 B2 | 9/2013 | Yang |
| 9,782,448 B2 | 10/2017 | Collins |
| 9,884,009 B2 | 2/2018 | Lin |
| 10,285,932 B2 | 5/2019 | Boland |
| 10,632,056 B2 | 4/2020 | Toomey |
| 10,695,287 B2 | 6/2020 | Robbins |
| 2020/0396961 A1* | 12/2020 | Zetouna ................. A23K 20/26 |

FOREIGN PATENT DOCUMENTS

WO   WO-2021149270 A1 * 7/2021

* cited by examiner

*Primary Examiner* — Kyle A Purdy
(74) *Attorney, Agent, or Firm* — Randal D. Homburg

(57) ABSTRACT

A topical skin treatment for the mitigation of various skin irritations and abnormal skin conditions, the composition and method for making the topical skin treatment providing a mixture of tea extracts from the snow mushroom, Reishi mushrooms, and other various organic ingredients in a range of constituent amounts to form a homogeneous liquid compound solution applied to the skin in liquid or aerosol form.

3 Claims, No Drawings

TOPICAL SKIN TREATMENT

I. BACKGROUND OF THE INVENTION

1. Field of Invention

A topical skin treatment for the mitigation of various skin irritations and abnormal skin conditions, the composition and method for making the topical skin treatment providing a mixture of tea extracts from the snow mushroom, Reishi mushrooms, and other various essential and exclusive organic ingredients in a range of constituent amounts to form a homogeneous liquid applied to the skin in liquid or aerosol form.

2. Description of Prior Art

A preliminary review of prior art patents was conducted by the applicant which reveal prior art patents in a similar field or having similar use. However, the prior art inventions do not disclose the same or similar elements as the present topical skin treatment composition and method of making the effective combination, nor do they present the material components in a manner contemplated or anticipated in the prior art.

Three prior art patents involve the mushroom known as Reishi, which is scientifically classified as Ganoderma Lucidum. In U.S. Pat. No. 10,695,287 to Robbins, an AMPK adenosine monophosphate-activated protein kinase, agonist is used to treat one or more human or animal medical conditions, one option for the AMPK agonist being Reishi is combined with biotin and Haematococcus pluvialis algae to create a supplement composition to support the health of skin, hair and nails, intended for oral consumption as a supplement in U.S. Pat. No. 10,632,056 to Toomey. In a third patent, U.S. Pat. No. 9,782,448 to Collins, Reishi is identified and categorized as a Chemotaxis pathway inhibitor, combined with at least one Histamine Receptor inhibitor, at least one Lipoxygenase pathway inhibitor, and at least one Cyclooxygenase pathway inhibitor to treat intact inflamed skin. None of these contain the other essential additives which are used in the present method and composition, especially noting the absence of snow mushrooms, scientifically classified as Tremella funciformis.

The snow mushroom has been used in at least four patented compositions and extracts disclosed herein. In U.S. Pat. No. 5,547,672 to Xiu, an extract of the snow mushroom is used in the manufacture of a pharmaceutical agent for treatments of wounds and skin injuries, delivered as a pure extract paste or in aerosol when diluted by water. A similar snow mushroom extract is presented as a skin wound healing agent when combined with an alginate, the extract removed by hot water from the snow mushroom forming a Tremella polysaccharide, in U.S. Pat. No. 8,524,271 to yang. This extract and combination is then delivered as a composite fiber, sponge or hydrogel. It is claimed that the snow mushroom, when combined with Dendrobium nobile, Viola tricolor, Ophiopogon japonicus and an oatmeal material, provide a moisturizing, anti-wrinkle and anti-allergic traditional Chinese medicine composition and preparation method thereof in U.S. Pat. No. 9,884,009 to Liu. Most recently, U.S. Pat. No. 10,285,932 to Boland, is used to treat hyperpigmentation and skin pigment disorders. It is also used to treat the eye area for reduction of laxity, puffiness and dark circles under the eye. None of these formulas have been tested, used or suggested that they be combined with Reishi to added effectiveness or other combined purpose.

II. SUMMARY OF THE INVENTION

Human skin is the largest organ in the human body. It provides protection for the body against injury, assists in regulating temperature, retains water and electrolyte balances, provides sensory alert for dangerous conditions and is primarily responsible for Vitamin D as a source. It also provides a protective shield to UV radiation. Billions of dollars are spent on maintaining healthy skin conditions and nurturing it to avoid the affects of aging, sun, complexion and overall health, especially in the cosmetic industry.

The skin has three layers including the epidermis, or outer layer, the dermis and the subcutaneous fat layer. Within the skin are included sebaceous glands, hair, capillaries, melanocytes and sweat glands, each item serving a function in the skin purpose and maintenance. The skin, though durable, is subject to injury, disease and allergic reactions wherein the skin is breached, inflamed, irritated or diseased. There are products on the market that maintain skin health, provide anti-inflammatory results, and repair injured skin. The immediate product is intended to address all three of these characteristics by a previously undisclosed exclusive combination of natural ingredients, which is non-toxic and could actually be ingested without harm, although intended for external use.

The primary objective of the invention is to provide a topical solution for skin care, skin health and skin maintenance and repair. A second objective is to provide for healthy skin care to minimize the effects of aging and skin deterioration. In doing so, several ingredients found in nature are combined to form the topical solution, which is delivered by topical application including liquid application, aerosol spray and nebulizer. The two vital ingredients are brewed liquid teas from the Reishi mushroom (Gandoderma lucidum) and the snow mushroom (Tremella fuciformis) as combined with other ingredients that allow these mushroom tea extracts to penetrate and to adhere to the skin.

III. DESCRIPTION OF THE DRAWINGS

There are no drawing submitted with this application.

IV. DESCRIPTION OF THE PREFERRED EMBODIMENT

A topical skin treatment to improve the condition of skin, expedite healing of wounds and skin irritation and to improve the appearance of the skin, combines several exclusive and essential organic ingredients to form a liquid solution. The primary solution constituents essentially include measured respective quantities of a tea extract from the Reishi Mushroom (Gandoderma lucidum), a tea extract from the Snow Mushroom, (Tremella fuciformis), organic Methylsulfonylmethane (MSM), organic Chitosan, Honey, natural Aloe Vera extract (Aloe), Cider Vinegar, preferably from pineapple, Bromolain, if the Cider Vinegar is not from pineapple, organic Quercetin Dihydrate, and water. The disclosed liquid must contain some quantity of each of these foregoing ingredients and may not contain anything other than those ingredients disclosed in order to provide the disclosed and predictable results.

The process for creating the solution involves the steps comprising boiling Reishi Mushroom powder in water for a period not to exceed 5 minutes and setting the tea extract aside. At the same time, the Snow Mushroom powder is boiled in water for a period not to exceed 5 minutes and setting the tea extract aside. Once cooled to tepid temperature (similar to drinkable hot tea), the remnant quantities of the two tea extracts are combined at a certain quantity and ratio.

Adding to the tea is a quantity of MSM, chitosan, honey, aloe extract, cider vinegar (preferably pineapple cider vinegar), Quercetin dihydrate, water, and Bromelain, if the cider vinegar is not from pineapple, pineapple already containing Bromelain. The complete solution is then blended to form a homogeneous liquid mixture.

The snow mushroom has been used for centuries in Eastern medicine. It is a potent anti-oxidant, anti-inflammatory and anti-aging fungus found in nature as a gelatinous basidiocarp growing as a parasite on trees. The Reishi mushroom has been used for centuries in Chinese and Japanese medicine as an herbal remedy, with studies showing that it produces anti-allergic, anti-oxidant, anti-tumor, anti-viral and anti-inflammatory properties. The tea extracts from these two mushrooms, combined for the first time in the disclosed combination, will demonstrate that they assist in skin health, recovery, maintenance, and healing, especially when combined with the other essential ingredients, which further enhance the effect, delivery and application of these healing mushroom extracts, with unanticipated effects not found in other distinctive compounds.

MSM is a permeable enhancement solvent know for its anti-bacterial properties. It is also a liquid skin permeability enhancer which transports liquids and solid materials through skin barriers into the capillaries in the inner skin layer. It can be found naturally in eggs, fish, lean meat and green plant materials, from which it can be extracted. It is also available commercially. Either form will work for this solution. Chitosan, or chiton, is an anti-microbial bioactive polymer which provides a matrix to maintain placement of the solution on the skin area where it is applied. It acts as a solidifying agent and also a binder for the solution. It can be found is the shells of lobsters, crabs, shrimp and other shellfish and is a known natural polysaccharide polymer, acting as a "glue" to bind the other ingredients together. Honey is also an ingredient which provides a "glue" to enhance skin adherence and bind the solution to the skin, also providing additional anti-oxidant effects to the solution.

The aloe gel is provided to nourish the skin and assist in skin healing where the solution is applied to wound care and healing. Aloe gel is known for hydrating skin and accelerating the regeneration of damaged skin. It has been used in Native American healing for centuries and is still widely used in homeopathic remedies. The Quercetin dihydrate is provided for anti-aging effects and to alleviate cellular senescence of dermal fibroblasts. Cellular senescence is a process resulting from a variety of stresses that leads to a state of growth arrest. It is provided as a skin restorative measure, lowers skin pain and sensitivity, is an anti-inflammatory, and is considered a plant flavonol. It can be found and extracted from broccoli, asparagus, capers, ginko, St. John's Wort and elder. It is also available commercially.

The final ingredient, other than water, is a cider vinegar. A preferred cider vinegar is pineapple cider, which contains natural bromelain, which is an enzyme used for pain and swelling, and is extracted from the skin and flesh of the pineapple. Where pineapple cider is not available, apple cider may be used, but must be supplemented with bromelain, since apples do not contain bromelain naturally. Bromelain has been shown to relieve swelling and expedite recovery of tissue due to its anti-inflammatory properties. It has been shown to decrease paid, reduce swelling and redness, minimize muscle aching from post-workout stress and aids in burn treatment. The cider lowers the pH of the solution intentionally, because most skin disease or ailments present an alkaline pH to the skin. The acid in the cider neutralizes this alkaline conditions, reducing the pH of the skin to alleviate the skin disease, kill infectious disease and irritants, and also to allow the other ingredients to optimize their effect and expedite resulting healing of the solution overall.

For the tea extract of the Reishi and Snow mushrooms, 2-6 grams of mushroom powder is added to approximately 220-275 grams of pure water, respectively in separate boiling vessels, wherein the mixture is boiled for at least 5 minutes. The mixtures are then removed from the heat and allowed to steep. The yield should result in a mixture of the two tea extracts are combined to form approximately 250-300 grams of tea extract at between 50 and 65% mushroom extract. To this extract solution, the remaining ingredients are added as follows:

MSM—between 6 and 10 grams;
Chitosan—between 1 and 5 grams;
Honey—between 9 and 15 grams;
Pineapple cider vinegar—between 7 and 12 grams or Apple cider vinegar and Bromelain powder of 5-7 grams/1-2 grams respectively;
Quercetin Dihydrate—between 0.5 and 2 grams; and
an additional 120 to 160 grams of purified water, the overall product yield optimally between 450 and 550 grams of compound solution, mixed until a homogeneous solution is the result. This resulting homogeneous compound solution would contain the following percentages of ingredients 50-60% combined mushroom extract;
1-3 MSM;
0.1-1.2% Chitosan;
1.5-5% Honey;
7.5-11% aloe gel;
1.0-3.0% Pineapple cider vinegar containing Bromelain or Apple cider vinegar with Bromelain added;
0.1-1.0% Quercetin Dihydrate; and
25-32% water, wherein the ingredients total 100%.

As previously indicated, the solution may be applied using a roller dispenser, a brush, a swab, an aerosol dispenser or a nebulizer, directly to any skin surface. Repeated use will present no harm and will only expedite a desired result. The homogenous compound solution is non-toxic and is not harmful if ingested, although ingestion is not recommended due to having no available information as to any direct health benefit, although each of the ingredients might have some health benefit when ingested, including the mushroom extracts which are considered by numerous homeopathic practitioners to have multiple internal healthy benefits as indicated in the prior art and multiple publications.

Results in pre-submission testing have included the following reported topical benefits including expedited healing to damaged skin, reduction in skin blemishes, improvement to skin health, improved skin texture and moisture content, reduction in skin irritation and itching, reduction in scar tissue, reduction of skin irritations including acne, psoriasis, eczema and recurrence of skin tags. It is also effective in reduction of dry skin providing hydration. Other benefits not yet known or studied may also present themselves and the compound solution has demonstrated no harmful effects during occasional or repeated use.

While the invention has been particularly shown and described with reference to a preferred embodiment of the compound solution thereof, it will be understood by those skilled in the art that changes in form and detail may be made therein without departing from the spirit and scope of the invention.

What is claimed is:

1. A homogenous liquid composition comprising:
   between 50-60% of a mushroom tea extract, the mushroom tea consisting of a mixture reishi mushroom; (Gandoderma lucidum) and snow mushroom (Tremella fuciformis);
   between 1-3% methylsulfonylmethane (MSM);
   between 0.1-1.2% chitosan;
   between 1.5-5% honey;
   between 7.5-11% natural Aloe Vera extract;

between 1.0-3.0% pineapple cider vinegar containing bromelain or apple cider vinegar with bromelain added;
between 0.1-1.0% quercetin dihydrate,
and between 25-32% purified water,
wherein the total of the listed ingredients equals 100%,
wherein the mushroom tea extract is made by a process of separately boiling powdered reishi mushrooms and snow mushrooms in purified water to form said respective tea extracts,
wherein the liquid composition improves the condition and appearance of skin and expedites healing of skin wounds and skin irritation when applied topically.

2. The liquid solution of claim 1, wherein the reishi mushroom tea extract is made by a process of combining 2-6 grams of reishi mushroom powder in 220-275 grams of purified water, boiling the mixture for at least 5 minutes and allowing the boiled mixture to cool.

3. The liquid solution of claim 1, wherein the snow mushroom tea extract is made by a process of combining 2-6 grams of snow mushroom powder in 220-275 grams of purified water, boiling the mixture for at least 5 minutes and allowing the boiled mixture to cool.

\* \* \* \* \*